(12) United States Patent
Nakamura et al.

(10) Patent No.: US 6,719,933 B2
(45) Date of Patent: Apr. 13, 2004

(54) METHOD FOR MANUFACTURING SEAMLESS CAPSULE

(75) Inventors: Takeshi Nakamura, Tokyo (JP); Kaoru Nemoto, Tokyo (JP); Isao Matsuda, Tokyo (JP); Hiroyuki Nakajima, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/168,027

(22) PCT Filed: Dec. 20, 2000

(86) PCT No.: PCT/JP00/09026

§ 371 (c)(1), (2), (4) Date: Sep. 25, 2002

(87) PCT Pub. No.: WO01/45635

PCT Pub. Date: Jun. 28, 2001

(65) Prior Publication Data

US 2003/0090015 A1 May 15, 2003

(30) Foreign Application Priority Data

Dec. 20, 1999 (JP) ............................................ 11-361260

(51) Int. Cl.⁷ ................................................ B29B 9/10
(52) U.S. Cl. ............................... 264/14; 264/13; 264/9; 264/4
(58) Field of Search ........................... 264/4, 9, 13, 14; 428/402.2; 424/16; 426/89

(56) References Cited

U.S. PATENT DOCUMENTS

| 5,223,185 A | * 6/1993 | Takei et al. ..................... 264/4 |
| 5,595,757 A | 1/1997 | Kiefer et al. ................ 424/451 |

FOREIGN PATENT DOCUMENTS

| JP | 59-46540 | 3/1984 |
| JP | 61-149150 | 7/1986 |
| JP | 4-322741 | 11/1992 |
| JP | 4-338230 | 11/1992 |

* cited by examiner

Primary Examiner—Rabon Sergent
Assistant Examiner—Thao Tran
(74) Attorney, Agent, or Firm—Morgan, Lewis & Bockius LLP

(57) ABSTRACT

A method of making a spherical seamless capsule formed by encapsulating a filler material such as a medicine with a capsule shell material shell such as gelatin. A liquid capsule shell material is stored in a tank at a low temperature, and supplied to a concentric multiple nozzle while it temperature is raised to a predetermined temperature upon being gradually heated while being transferred to the concentric multiple nozzle. This prevents deterioration in the capsule shell material and excessive decrease in its viscosity. When the liquid filler material and the capsule shell material flow out of the concentric multiple nozzle, their flows are cut by imparting a vibration thereto, to form a droplet in which the filler material and the capsule shell material are disposed at the center and on the outside, respectively. Such droplets are dropped into a curing liquid while in a dispersed state to cure the surface of the capsule shell material.

16 Claims, 2 Drawing Sheets

Fig.3A    Fig.3B    Fig.3C    Fig.3D

METHOD FOR MANUFACTURING SEAMLESS CAPSULE

TECHNICAL FIELD

The present invention relates to a method of making a spherical seamless capsule formed by encapsulating a filler material comprising a medicine, a flavor, a spice, a fragrance, and the like with a capsule shell material made of gelatin and the like.

BACKGROUND ART

For making such a seamless capsule, a concentric multiple nozzle comprising a center nozzle and an annular nozzle concentrically surrounding the center nozzle has conventionally been used. Namely, while a liquid filler material is caused to flow out of the center nozzle of the concentric multiple nozzle, a liquid capsule shell material is caused to flow out of the annular nozzle surrounding the center nozzle, thereby forming a composite flow having a concentric columnar form in which the capsule shell material flows so as to cover the outside of the filler material flow. The composite flow is sequentially cut from its front end, so as to form a droplet, which is then brought into contact with a curing liquid, thereby making a spherical seamless capsule in which the filler material is encapsulated with the capsule shell material.

However, there are cases where the above-mentioned conventional method of making a seamless capsule causes various defects in seamless capsules made thereby, for example, such as large eyes shown in FIG. 3A, eccentricity shown in FIG. 3B, deformation shown in FIG. 3C, and a bump shown in FIG. 3D.

It is an object of the present invention to provide a method of efficiently making a seamless capsule having no defects.

DISCLOSURE OF THE INVENTION

The inventors conducted various studies in order to achieve the above-mentioned object and, as a result, have found that the above-mentioned drawbacks occur due to the fact that there are cases where the liquid capsule shell material supplied to the concentric multiple nozzle does not have a desirable state or physical property. In particular, while the viscosity of the liquid capsule shell material is determined by temperature, there are cases where the viscosity becomes very low due to various reasons even when the capsule shell material supplied to the concentric multiple nozzle has a predetermined temperature.

Therefore, the present invention provides a method of making a seamless capsule formed by encapsulating a filler material with a capsule shell material, the method comprising a step of preparing a concentric multiple nozzle having a center nozzle and an annular nozzle concentrically surrounding the center nozzle; a step of storing a liquid filler material in a first tank; a step of storing a liquid capsule shell material at a predetermined first temperature in a second tank; a step of preparing a curing bath for storing a curing liquid adapted to cure the liquid capsule shell material by coming into contact therewith; a step of supplying the liquid filler material from the first tank to the center nozzle of the concentric multiple nozzle and supplying the liquid capsule shell material from the second tank to the annular nozzle of the concentric multiple nozzle; a step of forming a droplet by cutting a flow of the liquid filler material caused to flow out of the center nozzle and a flow of the liquid capsule shell material caused to flow out of the annular nozzle and flow about the flow of the filler material; and a step of bringing the capsule shell material of the droplet from the concentric multiple nozzle into contact with the curing liquid stored in the curing bath so as to cure the capsule shell material; wherein, while transferring the liquid capsule shell material from the second tank to the annular nozzle of the concentric multiple nozzle, the capsule shell material is gradually caused to raise temperature by heating so as to attain a predetermined second temperature, higher than the first temperature, when entering the annular nozzle. Preferably, the first temperature is a temperature at which the liquid capsule shell material stored in the second tank maintains a substantially constant viscosity.

Thus, the liquid capsule shell material stored in the second tank maintains a substantially constant viscosity. The heating of the capsule shell material is limited to a predetermined time during the transfer to the concentric multiple nozzle, whereas the predetermined second temperature is always attained at last, whereby the liquid capsule shell material flowing out of the concentric multiple nozzle yields a substantially constant viscosity. As a consequence, the physical property or state of the liquid capsule shell material flowing out of the concentric multiple nozzle becomes stable, whereby the ratio of occurrence of defects is greatly reduced.

Also, it will be effective if a double tube is prepared as a transfer tube for transferring the liquid capsule shell material between the second tank and the annular nozzle, and the heating of the capsule shell material is carried out by circulating the liquid capsule shell material through the inner tube of the double tube while circulating a heating fluid for heating the capsule shell material in an annular space between the inner and outer tubes in the double tube.

When the raising of temperature becomes insufficient, a heater having a spiral tube communicating with the inner tube of the double tube may be provided in the middle of the double tube, so as to carry out the heating of the capsule shell material by circulating the heating fluid for heating the capsule shell material about the spiral tube.

A vibration or vibrations may be imparted to the liquid filler material and/or liquid capsule shell material supplied into the concentric multiple nozzle, so as to cut the flow of liquid filler material and flow of liquid capsule shell material flowing out of the concentric multiple nozzle, whereby the droplet can be formed. As a consequence, the flows can be cut at a desirable position, whereby a droplet having a fixed size can reliably be formed.

The vibration may be applied by providing a movable wall as a wall portion defining a part of a flow path within the concentric multiple nozzle and vibrating the movable wall.

Preferably, droplets from the concentric multiple nozzle are dispersed in the curing liquid within the curing bath such that a droplet descending path and a next droplet descending path are horizontally distanced from each other. This broadens the gap between droplets in a substantially vertical direction, thereby preventing the droplets from attaching to each other to flocculate.

BRIEF DESCRIPTION OF THE DRAWINGS

FIGS. 3A, 3B, 3C, and 3D are explanatory views showing defects of seamless capsules.

BEST MODES FOR CARRYING OUT THE INVENTION

Figure 1:
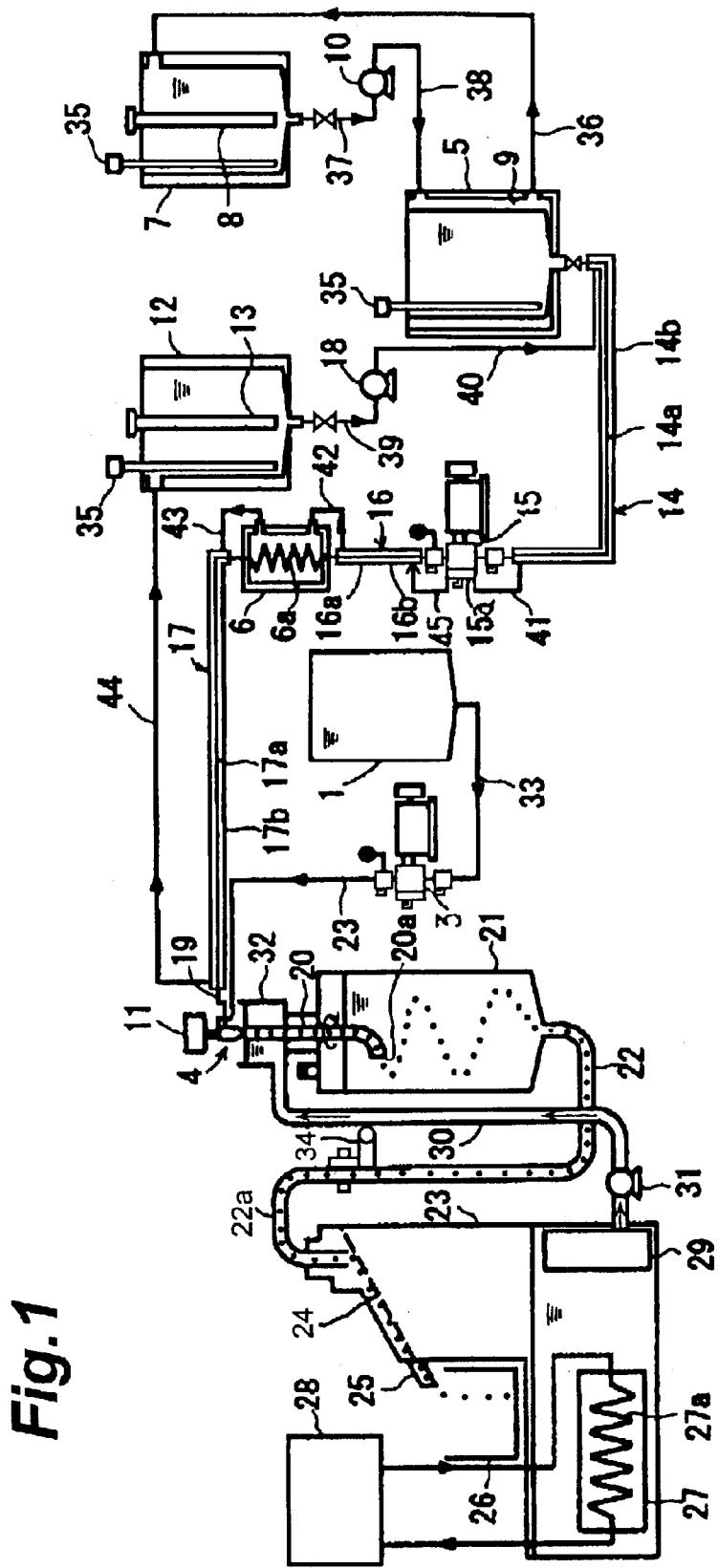
FIG. 1 is a schematic view showing a system for carrying out a method of making a seamless capsule in accordance with the present invention.
Figure 2:
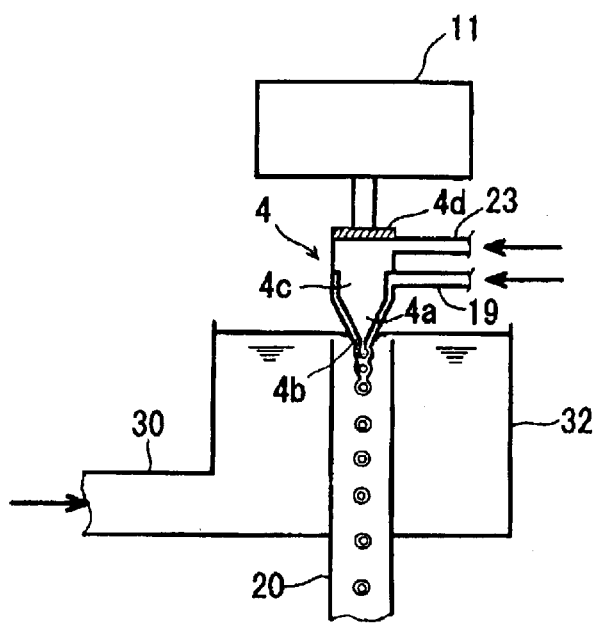
FIG. 2 is a partly enlarged view showing a concentric multiple nozzle used in the system of FIG. 1 and its vicinity.
Figure 2:
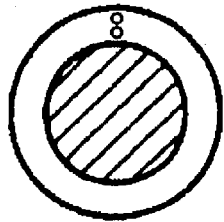
Figure 2:
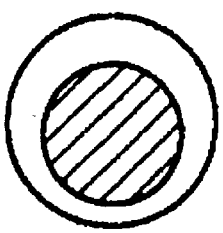
Figure 2:
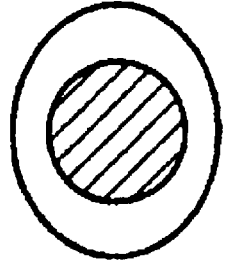
Figure 2:
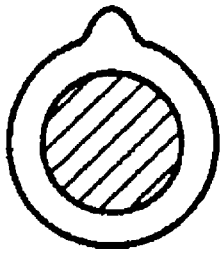

Now, a preferred embodiment of the present invention will be explained with reference to the drawings. FIG. 1 is schematically shows a system for carrying out the method of making a seamless capsule in accordance with the present invention, whereas FIG. 2 shows the configuration of a concentric multiple nozzle and its surroundings in the system under magnification.

In FIG. 1, numeral 1 indicates a filler tank 1 storing a liquid filler material (hereinafter referred to as filler liquid) comprising a medicine, a flavor, a spice, a fragrance, and the like. The filler liquid within the tank 1 is drawn by a variable discharge type filler pump 3 through a pipe 33, so as to be supplied to a concentric multiple nozzle 4 by way of a pipe 23. Since it is desirable for the flow of filler liquid to the concentric multiple nozzle 4 to be as stable as possible, the filler pump 3 is preferably of a type which imparts no pulsation to the flow.

On the other hand, numeral 5 in FIG. 1 indicates a gelatin tank (second tank) 5 storing a liquid capsule shell material (hereinafter referred to as gelatin solution) comprising a substance having a property of gelling from a sol state, for example, such as gelatin, agar, carrageenan, or alginic acid, or a substance such as a gum like guar gum or xanthan gum.

While being stored in the gelatin tank 5, the gelatin solution is heated by warm water circulating within a warm water jacket 9 disposed about the gelatin tank 5, so as to be maintained at a temperature (first temperature), e.g., 50° C., at which its physical property, such as viscosity in particular, can be kept constant.

The warm water having lowered its temperature in the process of circulating within the warm water jacket 9 is lead through a tube 36 into a first thermostat 7, where it is heated by a heater 8 so as to raise its temperature, and then circulates within the warm water jacket 9 again by way of a tube 37, a first warm water pump 10, and a tube 38.

The gelatin solution within the gelatin tank 5 is drawn through an inner tube 14a of a double tube 14 by a variable discharge type gelatin pump 15 which forms no pulsation in the flow, and is supplied to the concentric multiple nozzle 4 after passing through an inner tube 16a of a double tube 16, a spiral tube 6a of an intermediate heater 6, an inner tube 17a of a double tube 17, and a pipe 19 in this order.

Warm water acting as a heating fluid is introduced into an annular space between the inner tube 14a and outer tube 14b of the double tube 14 from a flow inlet provided at the end on the gelatin tank 5 side. The warm water is one heated by a heater 13 in a second thermostat 12, so as to maintain a constant temperature, and is supplied to the double tube 14 by a second warm water pump 18 by way of tubes 39 and 40. The warm water flowing between the inner tube 14a and outer tube 14b heats the gelatin solution flowing through the inner tube 14a of the double tube 14.

The warm water having flown into the circular space between the inner tube 14a and outer tube 14b flows into a warm water jacket 15a of a gelatin pump 15 by way of a tube 41, and then flows into an annular space between the inner tube 16a and outer tube 16b of the double tube 16 by way of a tube 45. In this process, the gelatin solution flowing through the inner tube 16a is heated by the warm water flowing between the inner tube 16a and outer tube 16b.

Subsequently, the warm water within the double tube 16 enters the intermediate heater 6 by way of a tube 42 and heats, while flowing about the spiral tube 6a, the gelatin solution flowing through the spiral tube 6a.

The warm water having flown out of the intermediate heater 6 enters an annular space between the inner tube 17a and outer tube 17b of the double tube 17 by way of a tube 43 and heats, in the process of flowing through this space, the gelatin solution flowing through the inner tube 17a. Thereafter, the warm water is caused to flow out of the double tube 17, and returns by way of a tube 44 into the second thermostat 12, where it is heated again.

Hence, the gelatin solution is heated by warm water while flowing through the transfer tubes 14a, 16a, 6a, 17a from the gelatin tank 5 to the concentric multiple nozzle 4, so that its temperature gradually rises from 50° C. to a predetermined second temperature, e.g., 80° C., and flows into the concentric multiple nozzle 4.

As shown in FIG. 2, the concentric multiple nozzle 4 comprises a center nozzle 4a opening downward and an annular nozzle 4b concentrically surrounding it, whereas front or lower end portions of the center nozzle 4a and annular nozzle 4b are immersed in a curing liquid within a capsule forming tube 20. The curing liquid is a liquid for curing the gelatin solution by coming into contact therewith, and can appropriately be selected from water, liquid paraffin, calcium solutions, and the like.

The upper portion of a chamber 4c within the concentric multiple nozzle 4 into which the filler liquid is introduced by way of the pipe 23 is provided with a movable wall 4d. The wall 4d is made of a flexible film or the like and defines a part of the wall portion of the chamber 4c. The movable wall 4d can be moved up and down by a vibrator 11, so as to impart vibrations having a predetermined period and amplitude to the filler liquid within the chamber 4c. As a consequence, the action of the movable wall 4d generates a downward propagating ripple in the filler liquid.

The filler liquid supplied to the concentric multiple nozzle 4 flows out downward from the center nozzle 4a, whereas the gelatin solution supplied to the concentric multiple nozzle 4 simultaneously flows out downward from the annular nozzle 4b into a form surrounding the flow of filler liquid. Then, the movable wall 4d is moved up and down at an appropriate timing, so as to generate a ripple in the filler liquid, whereby the filler liquid flowing out of the center nozzle 4a is cut. At this time, the vibrations are transmitted to the gelatin solution, whereby the gelatin solution flowing out of the annular nozzle 4b is cut. As a consequence, droplets having the filler liquid encupsulated with the gelatin solution are formed sequentially.

The droplets gradually become spherical because of their surface tension in the process of descending due to the gravity acting thereon and the curing liquid flowing down through the capsule forming tube 20. On the other hand, the gelatin solution on the surface of droplets is cooled is by coming into contact with the curing liquid and/or reacting with the curing liquid, thereby gradually curing.

The capsule forming tube 20 extends substantially vertically, whereas its lower portion curves horizontally. The free end of the curved portion has an opening 20a immersed in the curing liquid stored within the curing bath 21.

The capsule forming tube 20 is supported so as to be rotatable about its vertical axis, and is driven by a motor, which is not shown, to rotate. When the capsule forming tube 20 moderately rotates about the vertical axis, the curing liquid within the capsule forming tube 20 and its accompanying droplets flow out of the opening 20a, so that the droplets are dispersed onto the circumference of a circle having a diameter slightly greater than that of the locus of rotation of the opening 20a, and then moderately descend within the curing liquid, while the gelatin solution sufficiently cures during this process, whereby seamless capsules are formed.

The seamless capsules having descended to the bottom of the curing bath 21 enter a transfer tube 22 connected to an opening of the bottom of the curing bath 21 while being accompanied with the curing liquid, and are sent into a separator 23 through the transfer tube 22. In the upper portion within the separator 23, a sieve plate 24 made of a porous plate, a net, or the like is obliquely arranged. Since the sieve plate 24 has a mesh smaller than the outer diameter of seamless capsule, the curing liquid passes through the sieve plate 24 when the curing liquid and seamless capsules flow into the separator 23, thereby flowing in the bottom portion of the separator 23, so as to be stored there, whereas the seamless capsules roll on the sieve plate 24 and, by way of a chute 25, drop into a collecting container 26 so as to be stored there.

A cooler 27 is immersed in the curing liquid stored at the bottom portion of the separator 23, whereas a coolant cooled by a refrigerator 28 circulates through a heat exchanger tube 27a of the cooler 27. Therefore, while being stored in the bottom portion of the separator 23, the curing liquid is cooled upon heat exchange with the coolant circulating through the heat exchange tube 27a of the cooler 27.

The curing liquid is drawn out of the bottom portion of the separator 23 by way of a filter medium 29 made of silica gel or the like and, by way of a curing liquid tube 30 and a curing liquid pump 31, enters a reserve tank 32 installed about the capsule forming tube 20 and then flows over the upper edge of the capsule forming tube 20 into the tube 20.

The portion of transfer tube 22 attaining the highest position, i.e., an inverted U portion 22a, is lower than the level of the curing liquid within the reserve tank 32. When the inverted U portion 22a is moved up and down by a vertical movement unit 34 so as to adjust the difference between the inverted U portion 22a and the level of the curing liquid within the reserve tank 32, the flow rate of the curing liquid flowing through the transfer tube 22 by way of the curing bath 21 from the capsule forming tube 20 can be adjusted.

In FIG. 1, numeral 35 refers to a temperature sensor, and numeral 36 refers to a valve.

While the gelatin solution used for constructing a capsule shell of the seamless capsule lowers its viscosity as the temperature is higher, the gelatin solution itself deteriorates when placed for a long time at a high temperature, since molecules become smaller upon hydrolysis.

It has been known that, for forming a seamless capsule, the gelatin solution preferably has a viscosity of about 200 to 500 mPa·s upon flowing out of the concentric multiple nozzle 4.

When the gelatin solution is stored within the gelatin tank 5 for a long time at a high temperature of 80° C., for example, its molecular structure becomes so small that it deteriorates, and its viscosity greatly decreases. If it is caused to flow out of the concentric multiple nozzle 4 as it is, the shaping state of seamless capsule will deteriorate, thereby generating a large quantity of defects such as the eyes, eccentricity, and deformation shown in FIGS. 3A to 3D, and the strength of the capsule shell formed by curing the gelatin solution will decrease as well.

Therefore, it has conventionally been proposed to store the gelatin solution within the tank 5 at normal temperature, guide it into a heating bath, where its temperature is rapidly raised to about 80° C. upon heating with a heater, and then supply it to the concentric multiple nozzle 4. When raising the temperature of the gelatin solution from normal temperature to about 80° C. in this technique, however, not only local temperature deviations and local physical property changes are likely to occur in the gelatin solution, but also the temperature and viscosity of the gelatin solution supplied to the concentric multiple nozzle 4 are hard to keep constant.

In this embodiment, the gelatin solution is stored within the gelatin tank 5 at a temperature not affecting the physical property of the gelatin solution, which does not change the molecular structure at least, e.g., 50° C., whereby the viscosity during the storage can easily be kept constant.

The gelatin solution is heated while being transferred to the concentric multiple nozzle 4, whereby its temperature is gradually raised to 70° C. to 90° C. In this state, the gelatin solution is supplied to the concentric multiple nozzle 4, and is readily caused to flow out therefrom, whereby the temperature of gelatin solution flowing out of the concentric multiple nozzle 4 and its physical property such as viscosity can be kept constant.

Namely, the gelatin solution is gradually heated while moving through the inner tubes 14a, 16a, 17a of the double tubes 14, 16, 17 and the spiral tube 6a of the intermediate heater 6, whereby its temperature rises with a substantially constant temperature gradient, whereby local temperature deviations and physical property changes are prevented from occurring. The temperature of gelatin solution is raised only during the transfer from the gelatin tank 5 to the nozzle 4, which has a fixed time, whereby the gelatin solution exhibits a constant physical property at the time when it arrives at the concentric multiple nozzle 4. Since the heating during the transfer takes a short time, the excessive decrease in the viscosity of gelatin solution and the deterioration of gelatin solution can be prevented from occurring. As a result, defects such as eyes, eccentricity, deformation, and bumps of seamless capsules can be prevented from occurring, and high-quality seamless capsules can be made stably over a long time.

Since the intermediate heater 6 is interposed between the double tubes 16 and 17, the double tubes 14, 16, 17 have a shorter length, whereby the apparatus can be prevented from becoming larger in size. Also, since the gelatin solution is heated while moving within the spiral tube 6a of the intermediate heater 6, it does not stay within the intermediate heater 6. Namely, it is prevented from being heated for a long time.

Since the gelatin solution flows out of the concentric multiple nozzle 4 immediately after flowing therein, it hardly lowers its temperature, thereby flowing out with a desirable viscosity. This will contribute to making seamless capsules having a stable quality and size, together with the action of the movable wall 4d provided in the concentric multiple nozzle 4. Namely, while vibrations of the movable wall 4d are transmitted by way of the filler liquid to a composite flow made of the filler liquid and gelatin solution flowing out of the concentric multiple nozzle 4, so that the composite flow is sequentially cut from its front end, the viscosity of gelatin solution is kept substantially constant, whereby the cutting can reliably be carried out at a desirable position. Also, the amplitude and frequency of vibrations imparted to the movable wall 4d can easily be adjusted by the vibrator 11, whereby the size of droplet and the number of droplets per unit time can easily be regulated. As a result, the capacity of making seamless capsules can greatly be improved without generating defects in seamless capsules and enhancing fluctuations in the weight of seamless capsules and the amount of filler liquid.

Since the movable wall 4d is installed in the upper portion of the chamber 4c so as to define a portion of the chamber wall and is moved up and down, the ripple generated by the vibrations of movable wall 4d so as to propagate downward in the filler liquid can effectively be transmitted to the composite flow flowing out downward from the concentric multiple nozzle 4. Since it is sufficient for the vibrator 11 to vertically vibrate the movable wall 4d alone, a small-sized, inexpensive vibrator having a simple structure can be used as the vibrator 11, while the linking structure between the vibrator 11 and the movable wall 4d becomes simple, small in size, and inexpensive without imparting vibrations to its peripheral devices, whereby seamless capsules can be prevented from being adversely affected by detrimental vibrations which are unnecessary.

While favorable droplets are formed at the concentric multiple nozzle 4 as mentioned above, the droplets cure by coming into contact with the curing liquid, thereby accomplishing seamless capsules. Therefore, if the curing of droplets is insufficient, inconveniences such as the deformation of seamless capsules, adhesion and flocculation between seamless capsules, and breakage in the shell of seamless capsules may occur.

For sufficiently curing droplets, it is necessary to take a sufficient contact time with the curing liquid. If the droplets are caused to stay in the curing liquid in order to elongate the contact time, however, the droplets may attach to each other to flocculate, thereby breaking the shell of seamless capsules, deforming the seamless capsules, and so forth. If the flow rate of the curing liquid within the capsule forming tube 20 and curing bath 21 is slowed down, on the other hand, the descending rate of droplets will decrease as well. In this case, it is necessary to widen the gap between the droplets so as to prevent the droplets from coming into contact with each other. This will elongate the temporal interval between droplet dropping actions, thereby lowering the capacity of making seamless capsules. If the distance by which droplets are transported by the curing liquid is elongated, there will be fear of the apparatus becoming larger in size and raising its cost.

In this embodiment, droplets formed by cutting the composite flow flowing out of the concentric multiple nozzle 4 cure upon cooling in the process of moving through the capsule forming tube 20, curing bath 21, and transfer tube 22. Since the droplets descend while dispersing into the curing liquid within the curing bath 21 from the opening 20a of the capsule forming tube 20 moderately rotating so as to form a circular locus, the vertical gap between droplets becomes wider than that in the case where the droplets descend from the same position, whereby the possibility of droplets coming into contact with each other and flocculating upon adhesion decreases. Here, the dispersion means that one droplet descending path and a next droplet descending path are horizontally distanced from each other.

When a droplet is released from the opening 20a of the capsule forming tube 20 with a predetermined angle from the vertical direction, its vertical descending speed becomes slower, whereby the droplet can be caused to descend moderately. As a consequence, a sufficient contact time can be taken between the droplet and the curing liquid, which contributes to making a seamless capsule having no defects. Also, securing a contact time between the droplet and the curing liquid can shorten the distance by which the droplet is transported within the curing liquid, i.e., cause the capsule forming tube 20, curing bath 21, and transfer tube 22 to reduce their sizes and shorten their lengths, whereby the apparatus can be made smaller. Further, it contributes to improving the manufacturing efficiency, since the temporal interval between droplet dropping actions can be shortened.

Though a preferred embodiment of the present invention is explained in the foregoing, the present invention is not limited to the above-mentioned embodiment as a matter of course.

For example, while the depicted concentric multiple nozzle 4 has a double structure comprising the center nozzle 4a and the annular nozzle 4b surrounding the same, a triple or higher nozzle comprising the center nozzle 4a and a plurality of annular nozzles concentrically surrounding the same may be used as well. If a liquid is caused to flow out of only one of the center nozzle 4a and annular nozzle 4b, a seamless capsule having a single component can be made.

Though the movable wall 4d is provided in the upper portion of the concentric multiple nozzle 4 so as to impart vibrations to the filler liquid, vibrations may be imparted to the gelatin solution instead. Also, vibrations may be imparted to both of the filler liquid and gelatin solution in synchronization with each other.

The movable wall may have any form and structure as long as it can define a filler liquid flowpath and/or gelatin solution flow path within the concentric multiple nozzle 4, and is desirably provided in the vicinity of the concentric multiple nozzle 4.

Though the capsule forming tube 20 is rotated about its vertical axis in the shown embodiment, so as to cause the curing liquid to horizontally flow out of the opening 20a there of together with droplets, the opening of the capsule forming tube may be arranged at a position located near the outer periphery thereof in the upper portion of the liquid within the curing bath 21, so that the droplets horizontally flow out of the opening into the tangential direction of the curing bath 21. In this case, the curing liquid within the curing bath 21 can be swirled. Droplets carried by the swirling flow draw a spiral locus, so that the distance by which the droplets are transported within the curing bath elongates, whereby the gelatin solution sufficiently cures.

Further, the curing liquid may solely be caused to flow horizontally into the curing liquid stored within the curing bath 21 in a tangential direction, so as to swirl the curing liquid within the curing bath 21. In this case, it will be sufficient if the lower end of the concentric multiple nozzle 4 is immersed in the curing liquid within the curing bath 21 while omitting the forming tube.

Also, the composite flow from the concentric multiple nozzle 4 may be caused to flow out into the atmosphere, so as to form a droplet therein, and this droplet may be dropped onto the surface of the curing liquid swirling within the curing bath 21.

INDUSTRIAL APPLICABILITY

According to the present invention, seamless capsules having no defects can be made efficiently. Therefore, the present invention can widely be utilized in medical products and industries for making confectionery/food products and the like.

What is claimed is:

1. A method of making a seamless capsule formed by encapsulating a filler material with a capsule shell material, said method comprising:

a step of preparing a concentric multiple nozzle having a center nozzle and an annular nozzle concentrically surrounding said center nozzle;

a step of storing a liquid filler material in a first tank;

a step of storing a liquid capsule shell material in a second tank at a predetermined first temperature by which said liquid capsule shell material maintains a substantially constant viscosity;

a step of preparing a curing bath for storing a curing liquid adapted to cure said liquid capsule shell material by coming into contact therewith;

a step of supplying said liquid filler material from said first tank to said center nozzle of said concentric multiple nozzle and supplying said liquid capsule shell material from said second tank to said annular nozzle of said concentric multiple nozzle;

a step of forming a droplet by cutting a flow of said liquid filler material caused to flow out of said center nozzle and a flow of said liquid capsule shell material caused to flow out of said annular nozzle and flow about said flow of said filler material; and a step of bringing said capsule shell material of said droplet from said concentric multiple nozzle into contact with said curing liquid stored in said curing bath so as to cure said capsule shell material;

wherein, while transferring said liquid capsule shell material from said second tank to said annular nozzle of the temperature of the concentric multiple nozzle, the temperature of the capsule shell material is caused to rise with a substantially constant temperature gradient by heating during said transferring so as to attain a predetermined second temperature, higher than said first temperature, when entering said annular nozzle.

2. A method of making a seamless capsule according to claim 1, wherein a double tube comprising an inner tube and an outer tube surrounding said inner tube is prepared as a transfer tube for transferring said liquid capsule shell material between said second tank and said annular nozzle; and wherein said heating of said capsule shell material includes a step of circulating said liquid capsule shell material through said inner tube of said double tube while circulating a heating fluid for heating said capsule shell material in an annular space between said inner and outer tubes.

3. A method of making a seamless capsule according to claim 2, wherein a heater having a spiral tube communicating with said inner tube of said double tube is provided in the middle of said double tube; and wherein said heating of said capsule shell material includes a step of circulating said heating fluid for heating said capsule shell material about said spiral tube.

4. A method of making a seamless capsule according to one of claims 1 to 3, wherein a vibration is imparted to said liquid filler material and/or liquid capsule shell material supplied into said concentric multiple nozzle, so as to cut a flow of said liquid filler material and liquid capsule shell material flowing out of said concentric multiple nozzle, thereby forming said droplet.

5. A method of making a seamless capsule according to claim 4, wherein said vibration is imparted by using a movable wall as a wall portion defining a part of a flow path within said concentric multiple nozzle and vibrating said movable wall.

6. A method of making a seamless capsule according to claim 4, wherein said droplet from said concentric multiple nozzle is moderately dropped.

7. A method of making a seamless capsule according to one of claims 1 to 3, wherein droplets from said concentric multiple nozzle are dispersed into said curing liquid in said curing bath such that one droplet descending path and a next droplet descending path are horizontally distanced from each other.

8. A method of making a seamless capsule according to claim 7, wherein a vibration is imparted to said liquid filler material and/or liquid capsule shell material supplied into said concentric multiple nozzle, so as to cut a flow of said liquid filler material and liquid capsule shell material flowing out of said concentric multiple nozzle, thereby forming said droplet.

9. A method of making a seamless capsule according to claim 8, wherein said vibration is imparted by using a movable wall as a wall portion defining a part of a flow path within said concentric multiple nozzle and vibrating said movable wall.

10. A method of making a seamless capsule according to one of claims 1 to 3, wherein said droplet from said concentric multiple nozzle is moderately dropped.

11. A method of making a seamless capsule according to claim 1, wherein the transferring of said liquid capsule shell material from said second tank to said annular nozzle of said concentric multiple nozzle comprises moving said liquid capsule shell material through at least one passage associated with a heater.

12. A method of making a seamless capsule according to claim 11, wherein the moving of said liquid capsule shell material through at least one passage associated with a heater is performed without said liquid capsule material residing within said heater, thereby preventing said liquid capsule shell material from being heated for an undue amount of time.

13. A method of making a seamless capsule according to claim 1, wherein said heating of said capsule shell material is performed such that temperature of said capsule shell material rises with a substantially constant temperature gradient.

14. A method of making a seamless capsule according to claim 1, wherein, upon exiting said second tank, temperature of said liquid capsule shell material is raised only during transfer from said second tank to said concentric multiple nozzle.

15. A method of making a seamless capsule according to claim 1, wherein said transfer of said liquid capsule material from said second tank to said concentric multiple nozzle has a fixed time period whereby said liquid capsule material exhibits a constant physical property upon arrival at said concentric multiple nozzle.

16. A method of making a seamless capsule according to claim 1, wherein time of said heating is restricted so as to prevent occurrence of at least one of excessive decrease in viscosity of said liquid capsule material and deterioration of said liquid capsule material.

* * * * *